United States Patent [19]

Mikkelsen

[11] Patent Number: Plant 5,255

[45] Date of Patent: Jul. 10, 1984

[54] KALANCHOE PLANT NAMED DIGNITY

[75] Inventor: James C. Mikkelsen, Ashtabula, Ohio

[73] Assignee: Mikkelsens, Inc., Ashtabula, Ohio

[21] Appl. No.: 422,521

[22] Filed: Sep. 23, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A kalanchoe plant named Dignity, characterized by its excellent keeping quality, free branching and vigorous growth habits, well clustered, pink flowers, high floriferousness, and its adaptability to various pot sizes and to growth regulators.

1 Drawing Figure

The present invention relates to a new and distinct cultivar of kalanchoe plant, botanically known as kalanchoe, and referred to by the cultivar named Dignity. Dignity was discovered by me in Ashtabula, Ohio as a flower color mutation of the kalanchoe cultivar Sensation, disclosed in U.S. Plant Pat. No. 4,727. Dignity was discovered in early 1981 in flowering crops of 10 cm. pots of the parent cultivar. Other than flower color, the characteristics of Dignity are identical to the parent Sensation. Asexual reproduction by stem cuttings has shown that the unique features of this new kalanchoe are stabilized and are reproduced true to type in successive propagations.

The following characteristics in combination distinguish the new kalanchoe from other cultivated kalanchoes of this type known and used in the floriculture industry:

1. A soft light pink flower color when mature, but a generally light salmon shade in some florets when opening.
2. Dignity has excellent keeping qualities of the foliage and the flowers, both in the greenhouse and in the home.
3. Freely branching, with or without pinching, comparable to Sensation.
4. The same vigorous plant growth as Sensation.
5. Proper scheduling make the new cultivar suitable for production in 10 to 15 cm. pots.
6. After flower initiation, the growth of the terminal shoot slows down, resulting in approximately the same length of the terminal and side peduncles at flowering time, adding to the total flower placement.
7. During flower initiation, plants must be treated with B9 in all seasons to reduce peduncle elongation.
8. Flowering time is 10 weeks in summer to 14 weeks in winter after start of short days.
9. Flowers are the same size as Sensation.
10. Foliage is the same size and shape as Sensation.

The accompanying colored photograph taken June 1982 illustrates in perspective view the overall appearance of Dignity grown in a 10 cm. plastic pot, and showing the colors as true as it is reasonably possible to obtain in a colored reproduction of this type.

The following is a detailed description of Dignity based on plants produced under commercial practices in the greenhouses of Mikkelsens, Inc. at Ashtabula, Ohio. Color references are made to The Royal Horticultural Society Colour Chart except where general terms of ordinary dictionary significance are used.

PARENTAGE

A flower color mutation of kalanchoe cultivar Sensation.

PROPAGATION

Type cutting: Short tip cutting, with stems up to 2 cm. long.

Time to root: 10 days at 21° C. summer, 14 days at 21° C. winter.

Rooting habit: Many very fine roots, fibrous.

PLANT DESCRIPTION

Form: Short, compact, upright growth. Growing and scheduling practices can produce a small plant in a 10 cm. pot up to a larger plant in a 15 cm. pot.

Habit of growth: Rate of growth moderate for this type of plant. Generally, shoots are formed at every node.

Foliage description: Leaves simple, opposite. Frequently, leaves are asymmetrical, with a slight tendency to bend or twist.

(1) *Size.*—Average full grown leaf 130 mm. long×80 mm. wide. Full grown leaves have petioles.

(2) *Shape.*—Ovate to elliptic, apex obtuse, base attenutate.

(3) *Texture.*—Glabrous, coriaceous, succulent.

(4) *Margin.*—Sinuate to crenate.

(5) *Color.*—Young foliage, top side green 137B, under side green 138A. Mature foliage, top side darker than green 137A to yellow green 147A, under side green 137A-B.

FLOWERING DESCRIPTION

Flowering habits: Inflorescence of each shoot is formed by dichotomous branching, starting with opening of terminal flower of main axis, followed by terminal flowers of the side branches, continuing with subsequent development of branches in the inflorescence. Opening of new buds will continue for two months or more. Individual flowers last two weeks or more after opening.

Natural flowering season: Late January. Flowering time under controlled day length at 20° C. in summer is 10 weeks; in winter 14 weeks. Flowering time depends on temperature, light intensity and other growing conditions.

Flower bud description: Elliptical to oblong, up to 8 mm. long, developing to tubular as flower petals mature, sheathed with four green sepals. Corolla at maturity, 8 mm. long.

Flowers borne: Compound dichasial cyme on strong peduncles. Primary peduncle is 5 mm. in diameter, with peduncle length depending on growing conditions and B9 application; pedicels up to 8 mm. long.

Quantity of flowers: Highly floriferous. Main axis and side shoots have 100 or more flowers.

Petals:

(1) *Shape.*—Nearly round, with top slightly cuspidate.

(2) *Color.*—Top side when opening, red 37A-B, fading to red 55B on into 55C when inflorescence nears maturity; under side red 55C-D.

(3) *Number of petals.*—Four (4), united in corolla, salverform; petals 6 mm. in diameter, and total flower diameter 16 mm.

Reproductive organs:

(1) *Stamens.*—Eight (8) in number. Anther shape: flat, elliptical, color light brown; frequently, anthers are degenerated with dark brown color. Filament color: light green. Pollen color: yellow.

(2) *Pistils.*—Stigma shape: flat, crystalline, color greenish white. Style color: light green. Ovary: 4 celled, 6 mm. long, color green 143A.

DISEASE RESISTANCE

No diseases or adverse physiological problems observed to date. Cultivar is highly resistant to mildew.

I claim:

1. A new and distinct cultivar of kalanchoe plant known by the cultivar name Dignity, as described and illustrated, and particularly characterized by its soft light pink mature flower color, with a generally light salmon shade in some florets when opening, excellent keeping quality, free branching habit, highly floriferous and vigorous habit, and its adaptability to various pot sizes and growth regulators.

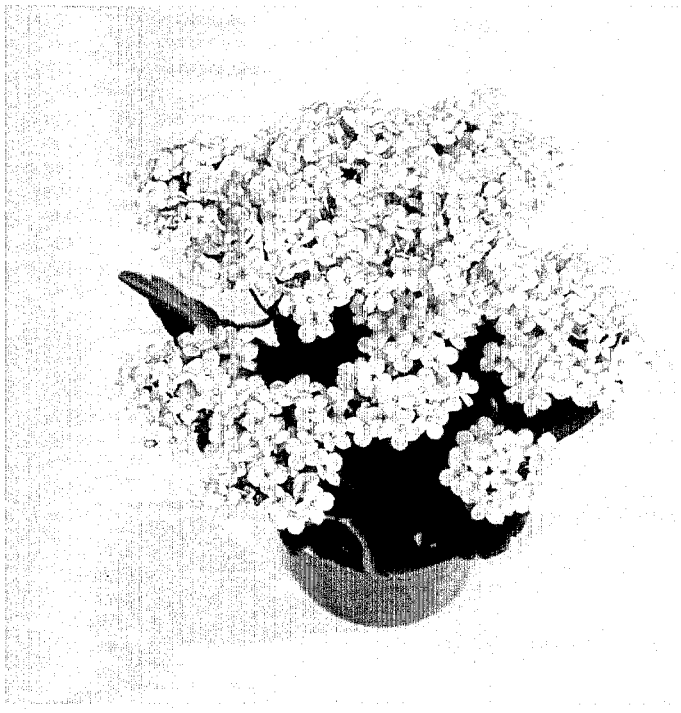

* * * * *